(12) United States Patent
McCauley et al.

(10) Patent No.: US 6,635,885 B2
(45) Date of Patent: Oct. 21, 2003

(54) APPARATUS FOR DELIVERING CALIBRATION COMPOUNDS TO MASS SPECTROMETERS AND METHOD

(75) Inventors: Edward B. McCauley, Cedar Park, TX (US); George B. Guckenberger, Austin, TX (US)

(73) Assignee: Thermo Finnigan LLC, San Jose, CA (US)

( * ) Notice: Subject to any disclaimer, the term of this patent is extended or adjusted under 35 U.S.C. 154(b) by 289 days.

(21) Appl. No.: 09/764,591

(22) Filed: Jan. 17, 2001

(65) Prior Publication Data

US 2002/0092979 A1 Jul. 18, 2002

(51) Int. Cl.⁷ .............................. H01J 49/04; H01J 49/24
(52) U.S. Cl. ........................ 250/428; 250/430; 250/435; 250/281; 250/282; 250/288
(58) Field of Search ................................. 250/428, 430, 250/435, 281, 282, 288

(56) References Cited

U.S. PATENT DOCUMENTS 5,237,175 A * 8/1993 Wells .......................... 250/288
6,460,401 B1 * 10/2002 Hoshino et al. ........... 73/23.35

* cited by examiner

*Primary Examiner*—Nikita Wells
(74) *Attorney, Agent, or Firm*—Dorsey & Whitney LLP

(57) ABSTRACT

An apparatus for delivering calibrant gas at selected flow rates to the ionization region of a mass spectrometer which employs capillary flow restrictors for metering the flow.

11 Claims, 1 Drawing Sheet

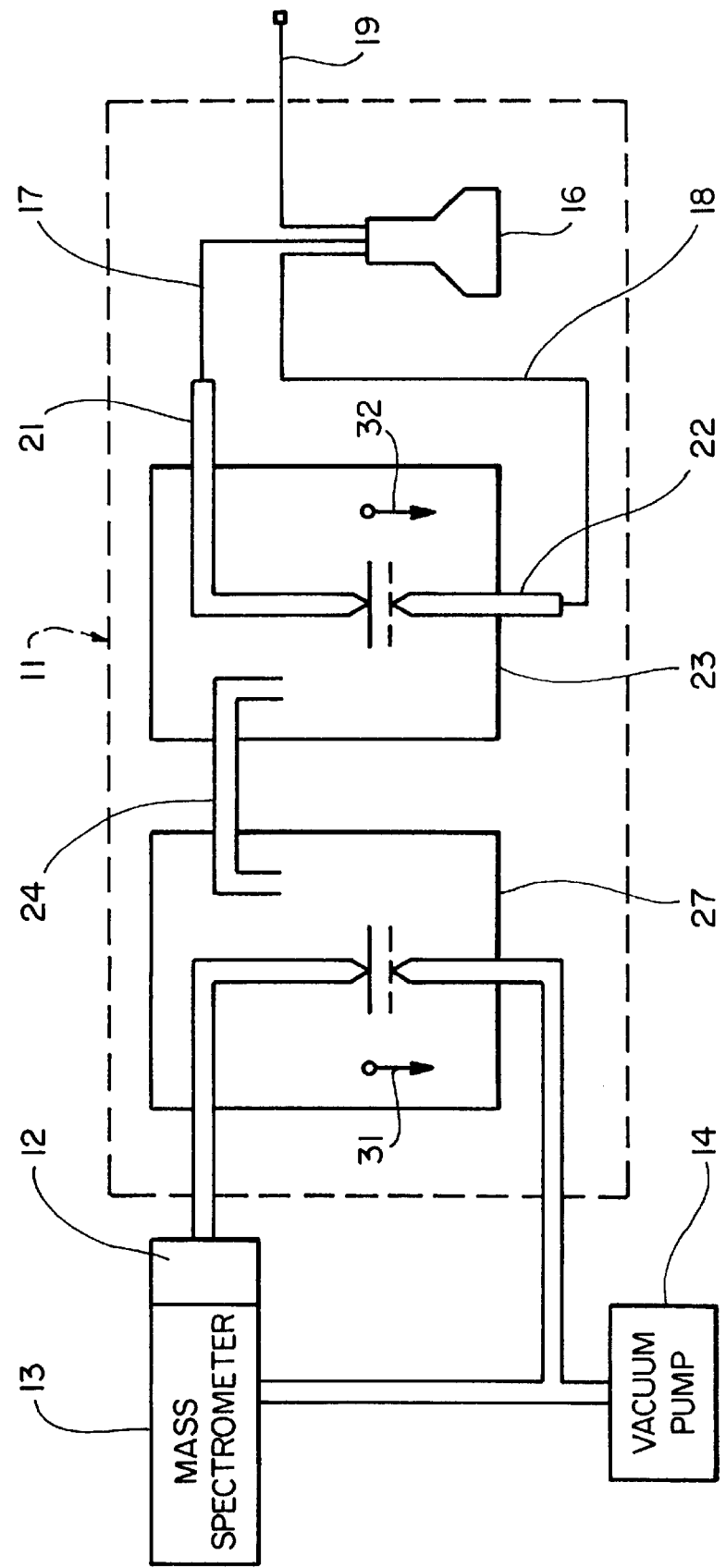

APPARATUS FOR DELIVERING CALIBRATION COMPOUNDS TO MASS SPECTROMETERS AND METHOD

BRIEF DESCRIPTION OF THE INVENTION

This invention relates generally to an apparatus for delivering gaseous calibration compounds to mass spectrometers, and more particularly to an apparatus in which metered volumes of different calibrants can be delivered to the ionization region of a mass spectrometer system.

BACKGROUND OF THE INVENTION

Traditional methods of introducing calibration compounds e.g. perfluorotributylamine to the ionization region of mass spectrometers involve the use of ball valves or needle valves. Instrument designs which feed the calibrant directly to the ionization region of the mass spectrometer typically utilize the needle valves due to the extremely small quantity (<4 ng/s) of calibrant required. Also, it is desirable to meter in a different amount of calibrant based on whether the instrument is operating in the EI or CI mode. Due to the close machining tolerances involved in the production of valves for this purpose, they tend to be costly. Other difficulties arising from these prior art metering methods include poor regulation due to variations in headspace pressure, poor regulation due to self-contamination (outgassing of calibrant from o-rings, valve seats and packings), lack of reproducibility when returning a valve to a previous setting, unknown volume delivery and poor equilibrium time.

OBJECTS AND SUMMARY OF THE INVENTION

It is an object of the present invention to provide an apparatus for delivering calibrant gas to the ionization region of a mass spectrometer at selected flow rates.

It is another object of the present invention to provide a delivery apparatus which uses calibrated restrictors and continuously pumped valves.

The foregoing and other objects of the invention are achieved by an assembly which employs calibrated restrictors connected between a calibrant gas source and the ionization region of a mass spectrometer through valves which can selectively connect the calibrant sources to the ionization chamber or to a vacuum pump.

BRIEF DESCRIPTION OF THE DRAWINGS

The foregoing and other objects of the invention will be more clearly understood from the following description when read in connection with the accompanying drawing.

DESCRIPTION OF THE PREFERRED EMBODIMENT

Referring to the FIGURE, the calibrant gas delivery apparatus 11 is shown connected to the ionization region 12 of a mass spectrometer 13, which is maintained at low pressure by a vacuum pump 14. The calibration gas delivery apparatus includes a calibrant vial 16 which supplies calibrant gas to flow restrictors 17 and 18. A flow restrictor 19 serves as a vent for the calibration gas vial, venting the vial to atmospheric pressure. Flow restrictors are capillary tubes having selected internal diameter and length to provide a predetermined calibrant gas flow rate into the ionization region. The flow rate is primarily dependent upon the internal diameter and length of the capillary restrictors. We have found that the flow rate through the capillary restrictors 17 and 18 is not measurably affected by the vacuum pressure in the ionization chamber or pump. Whether the pressure is $10^{-3}$ or $10^{-8}$ Torr the flow rate is substantially the same. In one example, capillary tubes having 0.025 mm internal diameter and 40 cm long was used for the restrictor 18 with the mass spectrometer operating in the electron ionization mode. A 0.050 mm internal diameter and 65 cm long capillary tubing was used for the other restrictor 17 when the mass spectrometer was operated in a chemical ionization mode. The vent restrictor was 0.25 mm internal diameter and 10 cm long.

The flow restrictors 17 and 18 are connected to two inputs 21 and 22 of a valve 23. The output 24 of the valve 23 is connected to the input of a valve 27. The valve 27 is selectively connected to either the flow restrictor 17 or 18 by the valve 23. The valve 27 is selectively connected to the vacuum pump 14 or the ionization chamber 12 of the mass spectrometer. There is a constant flow of calibrant, either to the ionization region or to the pump. This means that the gas delivery apparatus is continuously equilibrated. Referring to the FIGURE, valve 23 is shown set to connect the flow restrictor 18 through valve 27 to the vacuum pump 14. By activating the valve 27, as shown by the arrow 31, calibrant flowing through the restrictor 18 is supplied to the ionization chamber. With the valve 23 set in the direction of the arrow 32, calibrant flowing through the restrictor 17 can be selectively connected to the ionization chamber 12 or pump 14 by the valve 27.

In the example described above, with the restrictors' dimensions described above and the ionization region at full vacuum, the flow rate through the restrictors 17 and 18 was 0.04 cc/min and 0.004 cc/min, respectively. Other flow rates can be obtained by selecting capillary restrictors with different internal diameter and/or length. To assure that no air is drawn into the ion source, an inert gas purge may flow across the end of the vent restrictor 19.

Since the flow rate through the capillary restrictors varies with the fourth power of the internal diameter, the actual internal diameter must be determined in order to select a proper length for a given flow rate. The stated internal diameter from the vendor is "nominal", which cannot be relied upon for accuracy. One method of measuring the internal diameter is to select a length of capillary tubing of nominal internal diameter and introducing helium at a known pressure into one end of the selected length. The capillary tubing is maintained at a selected ambient temperature such as 25° C. The flow through the capillary is then determined using a flow meter. The internal diameter of the tubing can then be determined by calculation. Having determined the diameter of the tubing, a proper length for a restrictor can then be determined, assuming that the ionization region is at low pressure.

Thus, there has been provided a simple, economical apparatus for accurately delivering calibrant gas to the ionization chamber region of a mass spectrometer.

The foregoing descriptions of specific embodiments of the present invention are presented for the purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A gas delivery apparatus for delivering calibrant gas to the ionization chamber of a mass spectrometer which is evacuated by a vacuum pump comprising:
   a source of calibrant gas,
   a first valve for selectively connecting the source of calibrant gas to the ionization chamber of the mass spectrometer or to a vacuum pump,
   a first and second flow restrictor for selectively delivering calibrant gas from the source of calibrant gas at first and second flow rates, and
   a valve for selectively connecting the first or second flow restrictor to the first valve whereby gas is delivered to the ionization region or to the vacuum pump selectively at said first or second flow rate maintaining a constant flow of gas through the flow restrictor ensuring a continuously equilibrated system in order to provide a state of gas equilibrium with respect to surface absorption effects of the calibrant gas.

2. A gas delivery apparatus as in claim 1 in which the flow restrictors are capillary tubes having a preselected internal diameter and length for delivery of the calibrant gas at said first or second flow rates.

3. A gas delivery apparatus as in claims 1 or 2 in which said source of calibrant gas is a vial connected to said first and second restrictors and vented to atmospheric pressure through a flow restrictor.

4. A gas delivery apparatus as in claim 3 wherein an inert gas purge flows across the end of the flow restrictor.

5. A gas delivery apparatus as in claim 1 wherein there is a constant flow of calibrant gas either to the ionization chamber or the vacuum pump.

6. A gas delivery apparatus as in claim 1 wherein the gas delivery apparatus is continuously equilibrated.

7. The method of delivering calibrant gas to the ionization chamber which is evacuated by a vacuum pump of a mass spectrometer comprising the steps of:
   providing a source of calibrant gas;
   providing first and second capillary tubes of different preselected length and internal diameter to form flow restrictors,
   connecting the first and second flow restrictors to said source of calibrant gas, and
   selectively connecting one of the other of said first and second flow restrictors to said ionization chamber or to the vacuum pump to deliver calibrant gas at a flow rate which depends upon the diameter and length of the selected flow restrictor maintaining a constant flow of gas through the flow restrictor ensuring a continuously equilibrated system in order to provide a state of gas equilibrium with respect to surface absorption effects of the calibrant gas.

8. A gas delivery apparatus for delivering calibrant gas to the ionization chamber of a mass spectrometer which is evacuated by a vacuum pump comprising:
   a source of calibrant gas,
   at least one flow restrictor for delivering calibrant gas from the source of calibrant gas at a selected flow rate, and
   a valve for selectively connecting the flow restrictor to either the ionization chamber of the mass spectrometer or to the vacuum pump maintaining a constant flow of gas through the flow restrictor ensuring a continuously equilibrated system in order to provide a state of gas equilibrium with respect to surface absorption effects of the calibrant gas.

9. A gas delivery apparatus as in claim 8 in which the flow restrictor is a capillary tube having a preselected internal diameter and length for delivery of the calibrant gas at said selected flow rates.

10. A gas delivery apparatus as in claims 8 or 1 in which said source of calibrant gas is a vial connected to said restrictor and vented to atmospheric pressure through a vent restrictor.

11. The method of delivering calibrant gas to the ionization chamber which is evacuated by a vacuum pump of a mass spectrometer comprising the steps of:
   providing a source of calibrant gas;
   providing at least one capillary tube of preselected length and internal diameter to form a flow restrictor,
   connecting one end of the flow restrictor to said source of calibrant gas, and
   selectively connecting the other end of said restrictor to said ionization chamber or to the vacuum pump to deliver calibrant gas to said ionization chamber or vacuum pump at substantially the same flow rate which depends upon the diameter and length of the selected flow restrictor thus maintaining a constant flow of gas through the flow restrictor ensuring a continuously equilibrated system in order to provide a state of gas equilibrium with respect to surface absorption effects of the calibrant gas.

* * * * *